United States Patent
MacGregor

[11] Patent Number: 5,617,852
[45] Date of Patent: Apr. 8, 1997

[54] METHOD AND APPARATUS FOR NON-INVASIVELY DETERMINING BLOOD ANALYTES

[76] Inventor: Alastair R. MacGregor, Field House, Thriplow Road, Fowlmere, Royston, Hertfordshire SG8 7QT, England

[21] Appl. No.: 417,752

[22] Filed: Apr. 6, 1995

[51] Int. Cl.[6] ........................................ A61B 5/00
[52] U.S. Cl. ................................................ 128/633
[58] Field of Search ................................ 128/632, 633, 128/634, 665, 666, 667

[56] References Cited

U.S. PATENT DOCUMENTS 5,137,023 8/1992 Mendelson et al. ................ 128/633
5,355,880 10/1994 Thomas et al. ..................... 128/633
5,383,452 1/1995 Buchert ............................... 128/633

*Primary Examiner*—George Manuel
*Attorney, Agent, or Firm*—Choate, Hall & Stewart

[57] ABSTRACT

Method and apparatus for determining concentration of blood analytes non-invasively. Blood carrying tissue is illuminated with incident light at a selected frequency or frequencies. Light diffusely reflected from or transmitted through the tissue is collected, a portion of the reflected or transmitted light being frequency shifted with respect to the incident light by interaction with blood moving within the tissue. The frequency shifted portion of the light is analyzed to determine the concentration of blood analytes. Preferred embodiments are used to determine glucose concentration or measure the oxygenation of blood.

8 Claims, 1 Drawing Sheet

METHOD AND APPARATUS FOR NON-INVASIVELY DETERMINING BLOOD ANALYTES

BACKGROUND OF THE INVENTION

The invention disclosed here consists of a technique and apparatus for non-invasively measuring the concentration of blood analytes. Specifically, the technique enhances the accuracy of non-invasive optical spectroscopic blood analysis by rejecting the component of the diffusely reflected or transmitted optical signal which has not interacted with the blood. The invention is particularly suitable for home blood glucose testing but is applicable to other blood analytes and measurement setting (e.g. GP's office, hospital bedside or other hospital ward).

Blood is routinely analyzed during a wide range of medical diagnostic procedures. The concentration of certain biomolecules, such as glucose, urea, lactate and cholesterol provide important indicators of health. Blood samples are usually taken either using a venous puncture, if the sample is taken by a doctor or nurse, or using a spring loaded finger prick, if the sample is taken by the donor.

Physical withdrawal of a blood sample has a number of drawbacks:

- risk of infection to the donor and others who are in contract with the donor, blood sample or disposables (e.g. swabs) used during the withdrawal;
- inconvenience and embarrassment, particularly in the case where the donor draws their own blood;
- pain associated with skin puncture on a sensitive body site;
- risk of permanent tissue damage, such as the formation of callouses on fingers used repeatedly for withdrawals.

A non-invasive technique—one which does not require a blood sample to be withdrawn—for determining the concentration of blood analytes would overcome most if not all of the drawbacks listed above.

Previous approaches to non-invasive blood analysis have largely used optical spectroscopic techniques to penetrate the blood just below the tissue surface. The most successful and widespread of these techniques is pulse oximetry, which is used to determine blood oxygenation. However, more recently, effort has been focused on determining the concentration of blood glucose. This analyte is of particular interest because of the large home blood glucose testing market.

Non-invasive blood glucose determination has frequently used near infra-red radiation (wavelengths from 700 nm to 2500 nm) because of its ability to penetrate several millimeters into body tissues. However, diffuse reflectance or transmission measurement are complicated by the:

(1) weak absorption of glucose at these wavelengths, compared to the absorption of water and other tissue constituents;

(2) low concentrations of glucose in the blood (typically 3 mM to 7 mM);

(3) low volume fraction of blood in tissue (typically less than 10%).

Previous work in this area has used multi-variate spectral analysis techniques (e.g. partial least squares and principal components regression) in an attempt to overcome the complicating factors listed above. However, the accuracy which can be achieved by multi-variate analysis is hardly sufficient for glucose determination and it is desirable that the accuracy of this approach is increased.

The invention disclosed here allows the accuracy of non-invasive optical spectroscopic blood analysis to be increased by analyzing only the component of the diffusely reflected or transmitted optical signal which has interacted with the blood. The approach is fully compatible with near infra-red spectroscopy and multi-variate analysis.

SUMMARY OF THE INVENTION

The method for determining concentration of blood analytes non-invasively according to one aspect of the invention includes illuminating blood carrying tissue with incident light at a selected frequency or frequencies. Light diffusely reflected from or transmitted through the tissue is collected, a portion of this reflected or transmitted light being frequency shifted with respect to the incident light by interaction with blood moving within the tissue. The frequency shifted portion of the light is analyzed to determine concentration of blood analytes. In a preferred embodiment the blood analyte is glucose. In another embodiment, the method is utilized to determine the oxygenation of blood. It is preferred that the analyzed frequency shifted portion be shifted by more than a preselected amount. The analyzing step of the method of the invention may employ multi-variate spectral analysis techniques.

Another aspect of the invention is apparatus for determining concentration of blood analytes non-invasively. The apparatus includes a light source for generating incident light at a selected frequency or frequencies and a light detector for receiving light reflected from or transmitted through blood-containing tissue. Apparatus is provided for detecting a portion of the reflected or transmitted light which has been frequency shifted with respect to the incident light and means are provided for analyzing the frequency shifted portion of the light to determine the concentration of blood analytes.

DESCRIPTION OF THE PREFERRED EMBODIMENT

Figure 1:
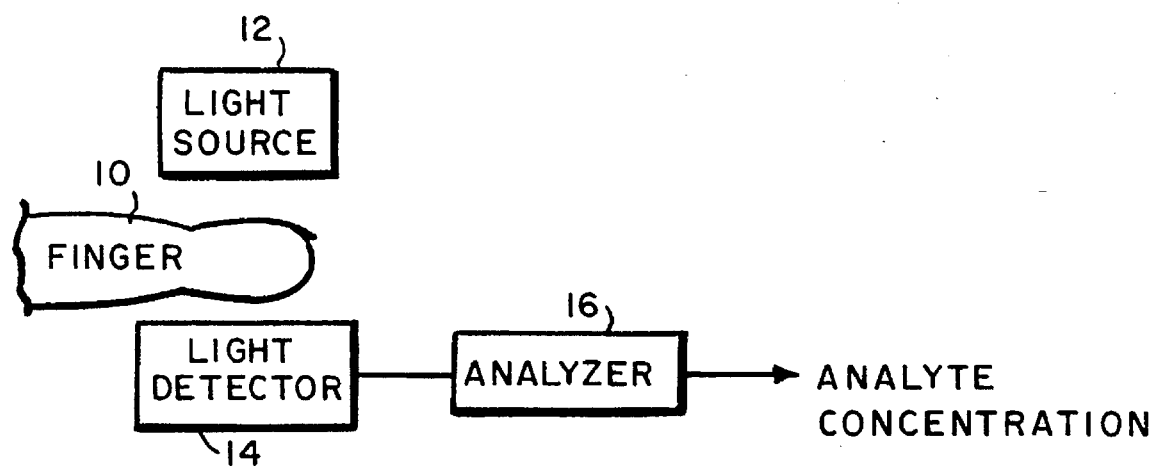
FIG. 1 is a schematic diagram illustrating the apparatus of the invention.

Laser Doppler blood flow measurement are used to determine tissue blood perfusion (e.g. the PeriFlux System 4000, Perimed). Laser Doppler systems illuminate blood carrying tissue with light, often carried to the tissue along an optical fiber. The light penetrates the tissue and, if it is scattered by moving blood cells, is frequency shifted by a small amount, typically 500 Hz for capillary blood flow. Multiple interactions with blood cells may lead to total frequency shifts of several kilohertz. See, "Principles of Laser-Doppler Flowmetry", R. F. Bonner and R. Nossal, Chapter 2 in "Laser-Doppler Blood Flowmetry", edited by A. P. Shephard and P. A. Oberg, Fluwer Academic Publishers, 1990.

Frequency shifts are typically detected by mixing the reflected signal, which may be collected by the same or additional optical fibers, on a detector with a non-frequency shifted signal so as to cause an electrical signal to be generated at the Doppler shift frequency. See, "Skin Blood Flow Measurements—A Review of Noninvasive Methods", A. R. S. Bukhari, J. Clin Eng, January/February 1993, 53–65; and "Spectral Analysis of Laser-Doppler Signals in Real Time Using Digital Processing", G. Dougherty, Med. Eng. Phys., 16, January 1994, 35–38. Alternatively, if the optical radiation is generated by a laser diode, the reflected signal can be focused back onto the laser diode where it generates an electrical signal proportional to the intensity of the Doppler shifted light.

Although the complex structure of skin makes absolute determination of blood velocity impossible, the mean blood velocity can be estimated by computing the power spectrum of the Doppler shifted signal.

The present invention uses the fact that much of the light diffusely reflected from body tissues which has interacted with the blood in that tissue will be Doppler shifted. Light which has interacted with the surrounding tissue will not be Doppler shifted. In determining the concentration of blood analytes, it is therefore advantageous to perform the analysis using only the Doppler shifted light.

As in the techniques described in the references set forth above, measurements of the diffusely reflected or transmitted light are made at a range of wavelengths and then analyzed, for example, using multi-variate spectral analysis techniques.

In a practical implementation of the invention, all light which is Doppler shifted by more than a certain frequency (e.g. 100 Hz) is used in the analysis. The threshold value selected may take into account Doppler shifts caused by effects other than blood flow, such as motion artifacts.

In addition to using the Doppler shift of the collected light, the signal may be further processed using independently gathered information on the time varying blood flow in the tissue. This information could be, for example, information on the blood pressure pulse gathered by electrical, optical or other sensors. Thus the signal could use Doppler shifted signals gathered during times when the tissue has maximum blood perfusion. The difference in Doppler shifted optical intensity between maximum and minimum perfusion can also be used to better assess which components of the signal are due to blood and to remove other artifacts, for example, due to motion.

The apparatus for determining concentration of blood analytes non-invasively according to the invention is shown in FIG. 1. A body part such as a finger 10 is placed between a light source 12 and light detector 14. An analyzer 16 receives a signal from the light detector 14 and analyzes only the frequency shifted portion of the detected light. The analyzer 16 then produces analyte concentration.

What is claimed is:

1. Method for determining concentration of blood analytes non-invasively comprising:

illuminating blood carrying tissue with incident light at at least one selected frequency;

collecting light diffusely reflected from or transmitted through the tissue, a portion of the reflected or transmitted light being frequency shifted with respect to the incident light by interaction with blood moving within the tissue; and analyzing the frequency shifted portion of the light to determine the concentration of blood analytes.

2. The method of claim 1 wherein the blood analyte is glucose.

3. The method of claim 1 utilized to measure the oxygenation of blood.

4. The method of claim 1 wherein the analyzed frequency shifted portion is shifted by more than a selected amount.

5. The method of claim 1 wherein the analyzing step employs multivariate spectral analysis techniques.

6. The method of claims 1, 2, 3, 4 or 5 wherein the incident light includes more than one selected frequency.

7. Apparatus for determining concentration of blood analytes non-invasively comprising:

a light source for generating incident light at at least one selected frequency;

a light detector for receiving light reflected from or transmitted through blood-containing tissue;

apparatus for detecting a portion of the reflected or transmitted light which has been frequency shifted with respect to the incident light; and means for analyzing the frequency shifted portion of the light to determine the concentration of blood analytes.

8. The apparatus of claim 7 wherein the light source generates incident light at more than one selected frequency.

* * * * *